(12) United States Patent
Watanabe

(10) Patent No.: US 9,034,158 B2
(45) Date of Patent: May 19, 2015

(54) SENSOR CARTRIDGE AND MEASURING DEVICE

(75) Inventor: Shinichi Watanabe, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 102 days.

(21) Appl. No.: 12/910,685

(22) Filed: Oct. 22, 2010

(65) Prior Publication Data

US 2011/0094881 A1 Apr. 28, 2011

(30) Foreign Application Priority Data

Oct. 26, 2009 (JP) ................. 2009-245817

(51) Int. Cl.
*G01N 33/487* (2006.01)
*G01N 27/327* (2006.01)

(52) U.S. Cl.
CPC ........ *G01N 33/4875* (2013.01); *G01N 27/3271* (2013.01); *G01N 33/48757* (2013.01)

(58) Field of Classification Search
CPC ................. G01N 33/4875; G01N 33/48757; G01N 27/3271
USPC ........ 204/400, 403.01–403.15; 221/186, 197, 221/220, 221; 600/300, 573, 576, 577, 600/345–347; 422/82.01–82.03
See application file for complete search history.

(56) References Cited

U.S. PATENT DOCUMENTS 5,741,634 A * 4/1998 Nozoe et al. ............. 204/403.03
2003/0089730 A1 5/2003 May et al.
2004/0176704 A1 9/2004 Stevens et al.
2007/0293790 A1 12/2007 Bainczyk et al.
2008/0066529 A1 3/2008 Zhong
2010/0196201 A1 8/2010 Sato

FOREIGN PATENT DOCUMENTS

| EP | 1 950 562 A2 | 7/2008 |
|---|---|---|
| EP | 1990634 A1 | 11/2008 |
| JP | H03-080353 U | 8/1991 |
| JP | 2510702 | 6/1996 |
| JP | H09-184819 A | 7/1997 |
| JP | 10-253570 | 9/1998 |
| JP | 2001-281199 | 10/2001 |
| JP | 2002-196003 A | 7/2002 |
| JP | 2002-310972 A | 10/2002 |
| JP | 2003-042994 A | 2/2003 |

(Continued)

OTHER PUBLICATIONS

The Extended European Search Report dated May 11, 2011; EP Application No. / Patent No. 10188773.5-1240 / 2315012.

(Continued)

*Primary Examiner* — Luan Van
*Assistant Examiner* — Maris R Kessel
(74) *Attorney, Agent, or Firm* — Studebaker & Brackett PC

(57) ABSTRACT

A sensor cartridge for supplying a sensor is used. The sensor cartridge includes a casing within which the plurality of sensors can be arranged, and that allows a sample to be introduced to a sensor located at a preset location, and a connection structure. The connection structure electrically connects an external device and a sensor electrode of the sensor located at the preset location. The casing is formed so as to be held by the external device when the external device and the sensor electrode of the sensor are electrically connected via the connection structure.

10 Claims, 17 Drawing Sheets

(56) References Cited

FOREIGN PATENT DOCUMENTS

| | | |
|---|---|---|
| JP | 2003-083927 A | 3/2003 |
| JP | 2003-215086 | 7/2003 |
| JP | 2004-3990 A | 1/2004 |
| WO | 02/08753 A2 | 1/2002 |
| WO | 2008/033435 A2 | 3/2008 |
| WO | 2008/056647 A1 | 5/2008 |

OTHER PUBLICATIONS

Examination Report Communication pursuant to Article 94(3) EPC issued by European Patent Office on May 16, 2012; EP Application No. 10 188 773.5-1240.

The second Office Action issued by the Chinese Patent Office on Aug. 4, 2014, which corresponds to Chinese Patent Application No. 201010526383.8 and is related to U.S. Appl. No. 12/910,685.

* cited by examiner

SENSOR CARTRIDGE AND MEASURING DEVICE

CROSS-REFERENCE TO RELATED APPLICATION

This application claims priority to Japanese Patent Application No. 2009-245817 filed on Oct. 26, 2009, the disclosure of which is incorporated in its entirety herein by reference.

BACKGROUND OF THE INVENTION

1. Field of the Invention

The present invention relates to a sensor cartridge for housing a sensor that is used for acquisition of living body numerical information, and a measuring device including such a sensor cartridge.

2. Description of the Related Art

Conventionally, in order to measure living body numerical information such as a blood glucose level, compact analytical sensors called biosensors are used. In general, a biosensor is a single-use device, and is set in a measuring device each time measurement is performed. After completion of measurement, the biosensor is then discarded together with a sample that has been measured. At the time of the next measurement, the user sets a new biosensor in the measuring device.

In general, biosensors are classified into biosensors using an electrochemical measurement method and biosensors using a colorimetric measurement method. Of these, the biosensors using an electrochemical measurement method (hereinafter, simply referred to as "biosensors") ordinarily include an inlet for introducing a sample into the biosensors and two or more electrodes. A sample introduced from the inlet is transferred to a position where the sample comes into contact with these electrodes, using capillary action or the like. In addition, the electrodes are electrically connected to connection terminals provided on the outer surface of the biosensor. Because of this configuration, it is necessary for the user to bring the connection terminals of the biosensor into contact with the corresponding terminals of the measuring device in a reliable manner, at the time of setting the biosensor in the measuring device.

However, there is a problem in that a situation tends to arise where the biosensor, because of its small size, is set in a wrong orientation or is not set in a predetermined position in a reliable manner especially in the case where the user has poor eyesight. For this reason, a sensor cartridge to which a plurality of biosensors are mounted and a measuring device including such a sensor cartridge has been proposed.

JP H10-253570A, JP 2001-281199A, and JP 2003-215086A disclose sensor cartridges that function as a sensor feeding device for successively supplying biosensors to a measuring device. Furthermore, a large number of biosensors are formed in the shape of a plate, and have been housed in advance in a stacked state in a container constituting the sensor cartridge. Additionally, the sensor cartridge housing the biosensors is attached within the casing of a measuring device.

At the time of measurement, the biosensors housed in the sensor cartridge are pushed out one by one by an arm provided within the measuring device, and the biosensor that has been pushed out is placed in a measurement position. Further, once the biosensor has been placed in the measurement position, electrodes provided within the measurement apparatus are moved to terminals of the biosensor and are connected to the terminals, bringing about a state where a sample can be measured. Thereafter, a sample is supplied into the biosensor, and measurement is carried out. The measured living body information is displayed on a display screen of the measuring device.

After completion of the measurement, the used biosensor is pulled out, and discarded. Then, at the time of the next measurement, an unused biosensor housed in the cartridge is newly placed automatically. In this way, it is thought that using the sensor cartridge and measuring device disclosed in JP H10-253570A, JP 2001-281199A, or JP 2003-215086A greatly improves the convenience for the user since it allows the user to carry out multiple measurements by simply setting the sensor cartridge.

JP 2510702Y discloses a sensor cartridge that has the function of successively supplying biosensors, and that is configured to function as a measuring device on its own, not just as a feeding device. Specifically, the sensor cartridge disclosed in JP 2510702Y is internally provided with a plurality of biosensors that are arranged in series, and only the biosensor at the head is exposed from the casing of the sensor cartridge. In addition, the sensor cartridge is connected to an external measurement apparatus via a distribution cable.

When the user performs measurement by using the biosensor located at the head while holding the sensor cartridge by hand, the data acquired with that biosensor is sent to the external measurement apparatus via the cable. Upon completion of the measurement, the user manipulates a slider that is provided in the sensor cartridge to push the used biosensor out, and then discards the biosensor. This slider manipulation also brings about a state in which a new biosensor has been set.

The measuring device disclosed in JP H10-253570A, JP 2001-281199A, or JP 2003-215086A is required to have complex mechanisms such as a mechanism for delivering biosensors contained in the sensor cartridge and a mechanism for connecting the electrodes of the measuring device to the connection terminals of the biosensors. Therefore, the measuring devices disclosed in these documents have the problem of high manufacturing costs. The measuring devices also have a problem in that they are susceptible to failure due to their complex mechanisms.

Furthermore, since the connection between the electrodes of the measuring device and the terminals of the biosensors is established by moving the electrodes of the measuring device by using an arm or the like, the positioning of the arm or the like may become inaccurate due to degraded parts, the environment of usage, a bug in the control software, and the like. If the positioning becomes inaccurate, there may be cases when the measurement error becomes large, or measurement is impossible, resulting in the problem of not being able to perform stable measurements.

Furthermore, biosensors are expected to be more compact in the future, and the required positioning accuracy will increase accordingly. Therefore, it is thought that the above-described problem of not being able to perform stable measurements will become even more significant with the size reduction of biosensors.

On the other hand, the mechanism of delivering the biosensors and the mechanism for connecting the connection terminals of the biosensor and the connectors of the sensor cartridge disclosed in JP 2510702Y are both simple. Accordingly, it is thought that the problems of high manufacturing costs, of susceptibility to failure, and of being not able to perform measurement stable can be solved by using the sensor cartridge disclosed in JP 2510702Y.

In the case of using the sensor cartridge disclosed in JP 2510702Y, however, it is necessary to connect the sensor cartridge and the measurement apparatus via the distribution cable as described above, and this results in the problem of poor handleability for the user.

SUMMARY OF THE INVENTION

An example of the object of the present invention is to solve the above-described problems, and provide a sensor cartridge that can prevent the structure of a measuring device from becoming complex and suppress a reduction in the measurement stability, while improving the handleability of sensors, and a measuring device including such sensor cartridge.

In order to attain the above-described object, a sensor cartridge according to one aspect of the present invention is a sensor cartridge for supplying a sensor, including: a casing within which the plurality of sensors can be arranged and that allows a sample to be introduced to a sensor located at a preset location; and a connection structure that electrically connects an external device and a sensor electrode included in the sensor located at the preset location, wherein the casing is formed so as to be held by the device when the device and the sensor electrode of the sensor located at the preset location are electrically connected via the connection structure.

According to the above-described feature, it is possible to make the sensor electrode electrically connectable to the external device (e.g., the device body or the like of the measuring device, which will be described later) while the sensor is housed in the casing of the sensor cartridge, and also to allow a sample to be introduced into the sensor. Additionally, the sensor cartridge is configured so as to be able to be held by the device. From these respects, it is possible to perform measurement of living body information using the sensor by simply attaching the sensor cartridge to the device, thus improving the handleability for the user. Furthermore, according to the above-described feature, it is possible to simplify the structure of the sensor cartridge and also the structure of the external device compared to those of their conventional counterparts, thus reducing the manufacturing costs. Moreover, since it is not necessary to perform the positioning of the electrodes each time measurement is carried out, it is also possible to perform stable measurements.

In the above-described sensor cartridge in a preferred mode of the invention, the casing is configured such that the plurality of sensors can be arranged in a line, and the connection structure electrically connects the device and the sensor electrode included in a sensor located at the head of the line. In this case, it is possible to simply the structure of the casing.

In the above-described sensor cartridge in another preferred mode of the invention, the casing is configured to allow the plurality of sensors to be arranged in a stacking direction, and to allow the sample to be introduced to a sensor located at the top or at the bottom, and the connection structure electrically connects the device and the sensor electrode of the sensor located at the top or at the bottom. In this case, it is possible to increase the efficiency in housing the sensors within the casing.

In the above-described sensor cartridge in a preferred mode of the invention, a member that presses the sensor located at the preset location is provided within the casing such that the sensor electrode of the sensor located at the preset location is pressed against part of the connection structure. According to this mode, it is possible to establish a solid connection between the sensor electrode and the connection structure, thus improving the connection stability.

In the above-described sensor cartridge in a preferred mode of the invention, the connection structure includes wiring provided on an outer surface of the casing, and the wiring is connected to the sensor electrode of the sensor located at the preset location. According to this mode, the connection structure can be realized with a simple configuration, and therefore it is possible to further reduce the manufacturing costs for the sensor cartridge.

In the above-described sensor cartridge in another preferred mode of the invention, the connection structure includes a conduction path penetrating through a wall of the casing, and is connected via the conduction path to the sensor electrode of the sensor located at the preset location. According to this mode, it is possible to shorten the wiring distance in the connection structure and reduce the wiring resistance, and therefore it is possible to improve the measurement accuracy.

In the above-described sensor cartridge in a preferred mode of the invention, the connection structure includes, within the casing, an electrode that comes into contact with the sensor electrode of the sensor located at the preset location, and an electrode for being connected to the device. According to this mode, it is possible to facilitate a further size reduction for the sensor cartridge. Furthermore, according to this mode, it is particularly preferable that one or both of the electrode that comes into contact with the sensor electrode of the sensor located at the preset location and the electrode for being connected to the device are configured to be elastically deformable by pressure. In this case, a solid connection is established by using an elastic force, and therefore it is possible to improve the connection stability.

In the above-described sensor cartridge in a preferred mode of the invention, the sensor cartridge further includes a delivery mechanism, and the delivery mechanism discharges the sensor located at the preset location, and causes a sensor placed adjacent to the discharged sensor to be located at the preset location. According to this mode, it is possible to easily discharge a used sensor and set a new sensor in a simple manner, thus further improving the handleability for the user.

Furthermore, in the above-described mode, the casing may include a sheet member on a principal surface of which the plurality of sensors can be placed, and the delivery mechanism may cause the sensor placed adjacent to the discharged sensor to be located at the preset location by moving the sheet member.

Preferably, the above-described sensor cartridge of the invention further includes, within the casing, an information presentation portion that presents information relating to the plurality of sensors housed in the casing. An example of the information relating to the sensors is information indicating a calibration curve suited for the sensors. In this case, the device can easily specify an appropriate calibration curve, and therefore it is possible, according to the above mode, to improve the measurement accuracy and shorten the measurement time.

In the above-described sensor cartridge in another mode of the invention, the casing is formed so as to be able to house at least part of the device when the device and the sensor electrode of the sensor located at the preset location are electrically connected via the connection structure.

Furthermore, in the above-described sensor cartridge in another mode of the invention, the casing is formed such that at least part of the casing is housed within the device when the device and the sensor electrode of the sensor located at the preset location are electrically connected via the connection structure.

In the above-described sensor cartridge in another mode of the invention, the casing includes an opening that allows the sample to be introduced to the sensor located at the preset location.

In order to achieve the above-described object, a measuring device according to one aspect of the invention is a measuring device for measuring living body numerical information by using a sensor, including: a sensor cartridge that supplies the sensor; and a device body that holds the sensor cartridge, wherein the sensor cartridge includes: a casing within which the plurality of sensors can be arranged, and that allows a sample to be introduced to a sensor located at a preset location; and a connection structure that electrically connects the device body and a sensor electrode included in the sensor located at the preset location, the casing is formed so as to be held by the device body when the device body and the sensor electrode of the sensor located at the preset location are electrically connected via the connection structure, and the device body includes an electrode that comes into contact with part of the connection structure when the device body holds the sensor cartridge.

As described above, with the sensor cartridge and the measuring device according to the present invention, it is possible to prevent the structure of the measuring device from becoming complex and suppress a reduction in stability of the measurement, while improving the handleability of sensors.

These and other objects, features, aspects and advantages of the present invention will become more apparent from the following detailed description of the present invention when taken in conjunction with the accompanying drawings.

BEST MODE FOR CARRYING OUT THE INVENTION

Embodiment 1

Figure 1:
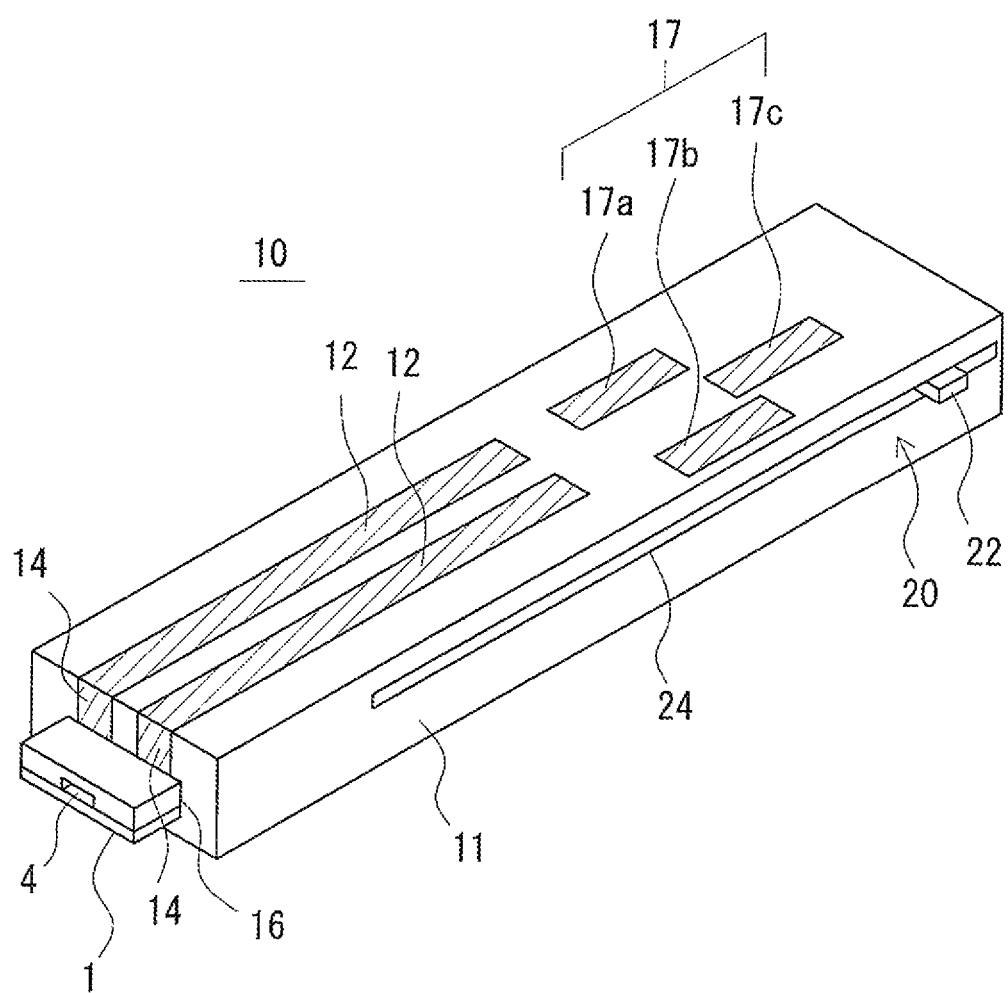
FIG. 1 is a perspective view showing the appearance of a sensor cartridge according to Embodiment 1 of the present invention.
Figure 2A:
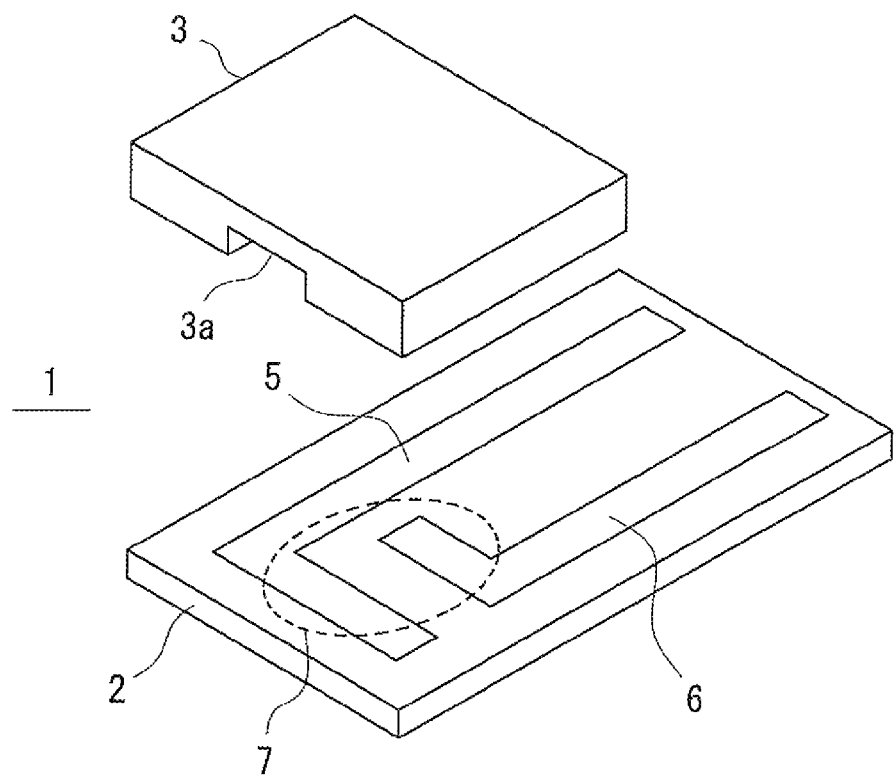
FIG. 2A is an exploded perspective view of an example of the sensor used in Embodiment 1 of the invention.
Figure 2B:
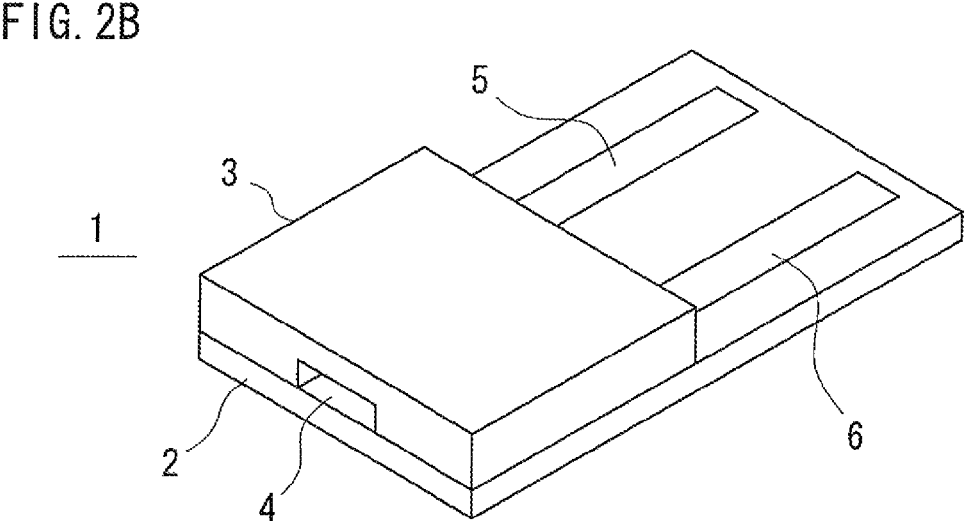
FIG. 2B is an assembly diagram showing the sensor in FIG. 2A.
Figure 3:
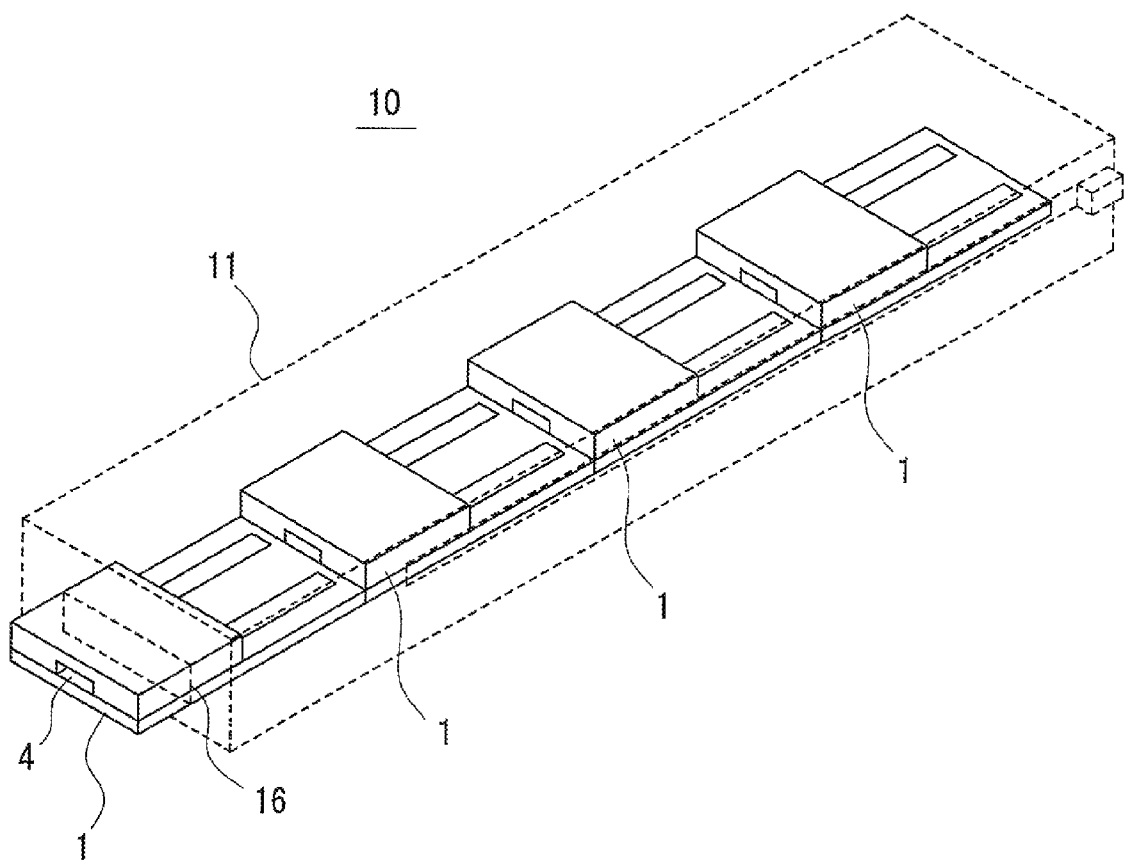
FIG. 3 shows a state in which the sensor shown in FIGS. 2A and 2B is housed in the sensor cartridge.

In the following, a sensor cartridge 10 and a measuring device 30 according to Embodiment 1 of the present invention will be described with reference to FIGS. 1 to 6. FIG. 1 is a perspective view showing the appearance of a sensor cartridge according to Embodiment 1 of the present invention. FIG. 2A is an exploded perspective view of an example of the sensor used in Embodiment 1 of the invention. FIG. 2B is an assembly diagram showing the sensor in FIG. 2A. FIG. 3 shows a state in which the sensor shown in FIGS. 2A and 2B is housed in the sensor cartridge.

Figure 4:
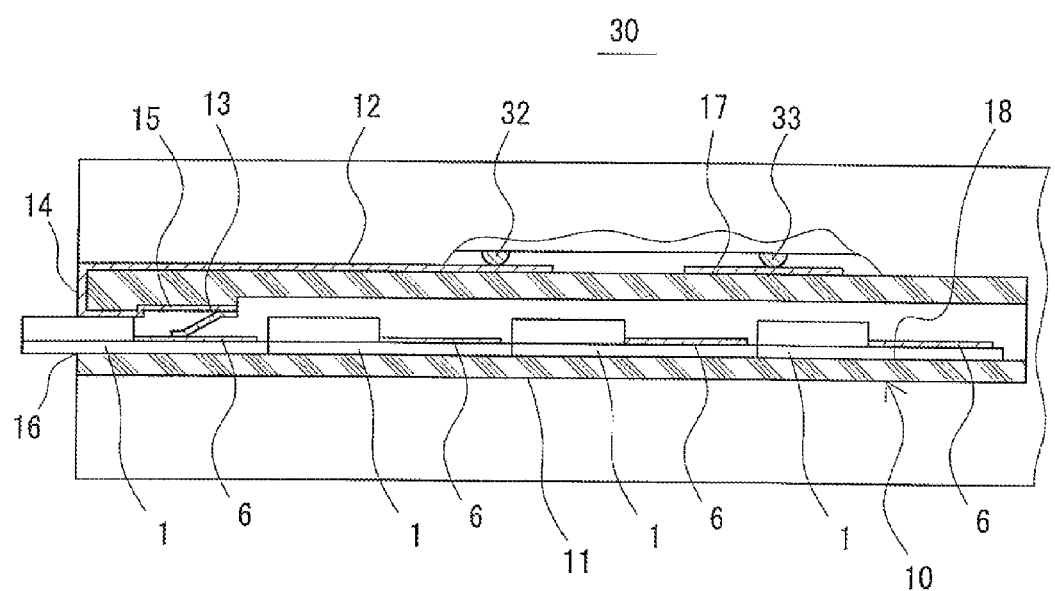
FIG. 4 is a cross-sectional view showing the internal configuration of the sensor cartridge and a measuring device according to Embodiment 1 of the invention.
Figure 5:
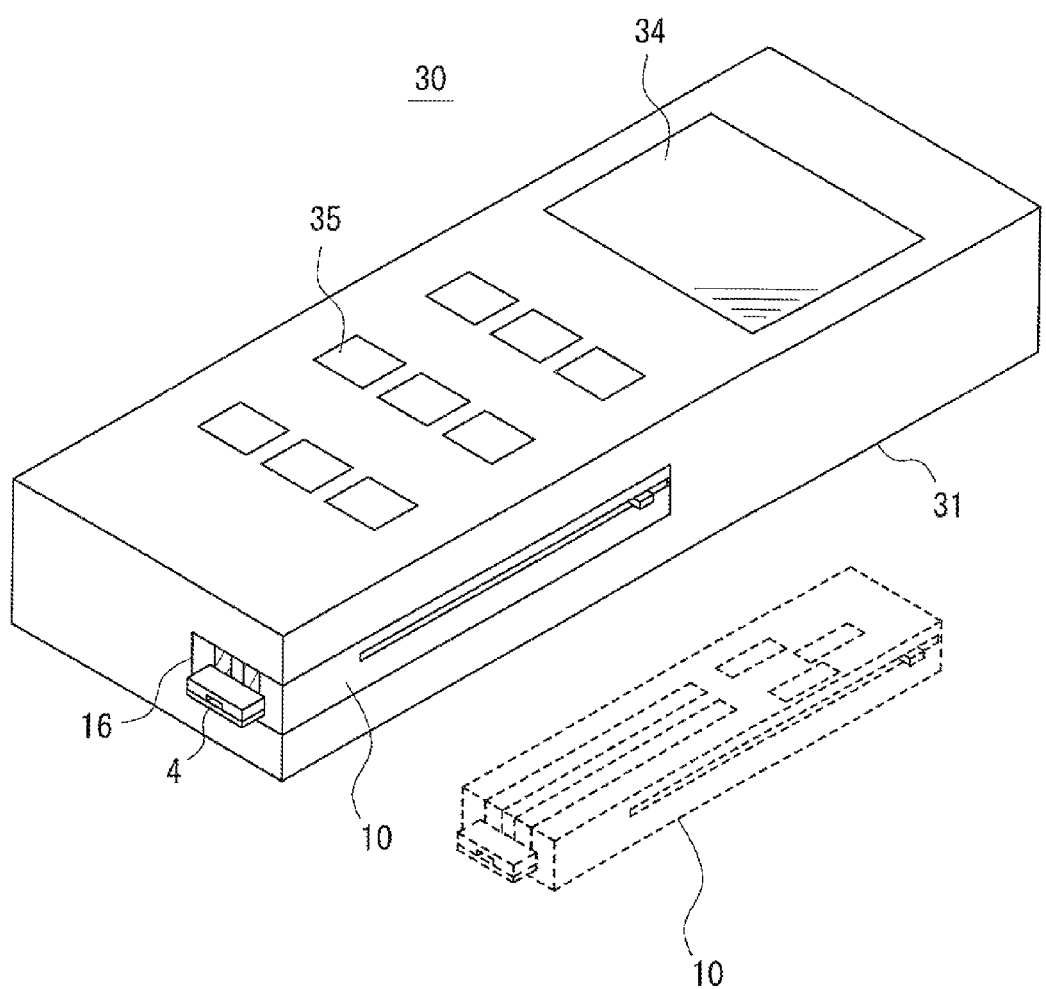
FIG. 5 is a perspective view showing the appearance of the measuring device according to Embodiment 1 of the invention.
Figure 6:
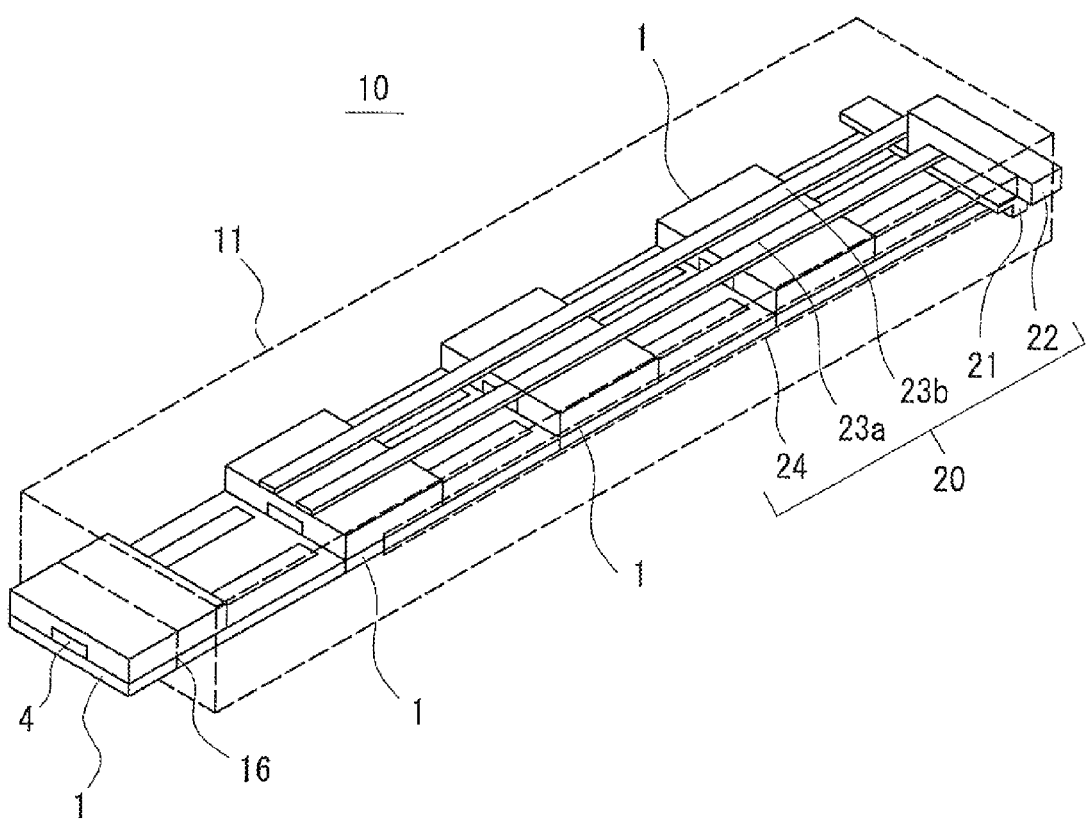
FIG. 6 is a perspective view showing a delivery mechanism provided in the sensor cartridge according to Embodiment 1 of the invention.

FIG. 4 is a cross-sectional view showing the internal configuration of the sensor cartridge and the measuring device according to Embodiment 1 of the invention. FIG. 5 is a perspective view showing the appearance of the measuring device according to Embodiment 1 of the invention. FIG. 6 is a perspective view showing a delivery mechanism provided in the sensor cartridge according to Embodiment 1 of the invention.

The sensor cartridge 10 shown in FIG. 1 according to Embodiment 1 is a cartridge used for supplying a sensor 1 to a measuring device (see FIG. 4). As shown in FIGS. 2A and 2B, the sensor 1 includes sensor electrodes 5 and 6, and a sample inlet 4.

Further, the measuring device 30 shown in FIG. 5 according to Embodiment 1 is a device that measures living body numerical information by using the sensor 1. Specifically, the measuring device 30 is, for example, a glucose meter, a lactate meter, a ketone body measuring device, a lipid measuring device, or the like.

As shown in FIG. 1, the sensor cartridge 10 includes a casing 11 (see FIG. 3) within which a plurality of sensors 1 can be arranged, and a connection structure. The casing 11 is formed so as to allow a sample to be introduced into a sensor located at a preset location. In Embodiment 1, the casing 11 includes an opening 16 for exposing an sample inlet 4 of the sensor 1 located at a preset location, as shown in FIGS. 1 and 3.

The connection structure electrically connects an external device and the sensor electrodes (see FIGS. 2A and 2B and 3) of the sensor located at a preset location within the sensor cartridge 10. In Embodiment 1, the external device is a device body 31 (see FIG. 5) of the measuring device 30. Also, in Embodiment 1, the connection structure includes wiring 12 provided on the outer surface of the casing 11, internal electrodes 13 (see FIG. 4) provided within the casing 11, and wiring 14 and 15 that connect the wiring 12 and the internal electrodes 13.

Further, as shown in FIG. 4, the internal electrodes 13 are placed so as to come into contact with the sensor electrodes 5 and 6 (in FIG. 4, the electrode 5 is not shown) of the sensor 1 located at a preset location. The internal electrodes 13 are electrically connected to the wiring 12 via the wiring 15 and 14. Although only the internal electrode 13 that comes into contact with the sensor electrode 6 is shown in the example shown in FIG. 4, an internal electrode 13 that comes into contact with the sensor electrode 5 as well is actually provided.

In Embodiment 1, as shown in FIG. 3, a plurality of sensors 1 are arranged in a line, and the preset location is set to the head of the line. Further, as shown in FIG. 4, the internal electrodes 13 are placed so as to come into contact with the sensor electrodes 5 and 6 of the sensor 1 located at the head of the line.

As shown in FIG. 5, the measuring device 30 includes the sensor cartridge 10 and the device body 31 that holds the sensor cartridge 10. The device body 31 holds the sensor cartridge 10 such that the opening 16 provided in the casing 11 of the sensor cartridge 10 is exposed to the outside of the device body 31.

Further, as shown in FIG. 4, the device body 31 is internally provided with electrodes 32 and 33. Of these, the electrode 32 is placed so as to come into contact with the wiring 12 of the sensor cartridge 10 when the device body 31 holds the sensor cartridge 10. The electrode 33 will be described later. In FIG. 4, the sensor cartridge 10 is shown in cross section, whereas only part of the device body 31 is shown in cross section for the measuring device 30. As shown in FIG. 5, the device body 31 is provided with a display screen 34 for displaying a measurement result and an operation button 35.

As described above, according to Embodiment 1, it is possible to electrically connect the electrodes 5 and 6 of the sensor 1 to the device body 31 of the measuring device 30 and also to introduce a sample into the sensor 1, while the sensor 1 is housed in the casing 11 of the sensor cartridge 10. Furthermore, electrical connection to the sensor 1 can be ensured for the device body 31 by simply placing the electrode 32 in a predetermined position such that the electrode 32 can connect to the wiring 12 of the sensor cartridge 10, and therefore the device body 31 can perform measurement of living body information. Thus, according to Embodiment 1, it is possible to prevent the structure of the measuring device 30 from becoming complex and suppress a reduction in stability of the measurement, while improving the handleability of the sensor 1.

Here, the configurations of the sensor cartridge 10 and the measuring device 30 according to Embodiment 1 and the structure of the sensor 1 used in Embodiment 1 will be described in further detail. First, the structure of the sensor 1 will be described in detail.

As shown in FIGS. 2A and 2B, the sensor 1 includes a sensor substrate 2 and a cover 3. The sensor substrate 2 is provided with a pair of electrodes 5 and 6. A sample 7 is introduced between one end of the electrode 5 and one end of the electrode 6. Further, the other end of the electrode 5 and the other end of the electrode 6 are in contact with and electrically connected to the internal electrodes 13 of the sensor cartridge 10.

The cover 3 is placed so as to be bonded to the sensor substrate 2. Additionally, a groove 3a is formed in the cover 3, and the groove 3a forms the sample inlet 4 when the cover 3 and the sensor substrate 2 are bonded together. Note that the structure of the sensor 1 shown in FIGS. 2A and 2B is an example, and sensors having other structures can be used in Embodiment 1.

Further, although not shown in FIGS. 2A and 2B, a reagent corresponding to the type of sample is placed at the portion on the sensor substrate 2 where the sample 7 is to be introduced. For example, in the case when the measuring device 30 is a glucose meter and the sample is blood, glucose oxidase and glucose dehydrogenase, which react with glucose in blood, can be used as the reagents. Also, a mediator is placed between these enzymes and the electrodes for the purpose of performing the exchange of electrons. For example, an electron transfer substance can be used as the mediator, and specific examples thereof include a ruthenium complex, an iron complex, and an organometallic complex.

When a voltage is applied between the electrode 5 and the electrode 6 in the case when the sample is blood, the glucose contained in the sample is oxidized by the enzyme, and the resulting electrons are transferred to the electrodes by the mediator. Therefore, the current flowing between the electrode 5 and the electrode 6 is proportional to the glucose amount in the sample. That is, the value of current flowing between the electrode 5 and the electrode 6 changes according to the glucose amount. The measuring device 30 detects this current value via the internal electrodes 13 and the wiring 12, and calculates the blood glucose level by fitting the detected current value to a calibration curve that has been prepared in advance.

Further, in Embodiment 1, the wiring 12 of the sensor cartridge 10 functions as electrodes for connecting to the device body 31 (see FIGS. 1 and 4). The wiring 12 is formed by attaching thin films or foils of metal onto the surface of the casing 11, or by forming films of a metallic material by vapor deposition, plating, or the like.

Further, in Embodiment 1, one end of the wiring 12 reaches the opening edge of the opening 16, and is connected to the wiring 14 at that opening edge. The wiring 14 is provided on the side of the casing 11 on which the opening 16 is provided. Further, the wiring 15 is provided within the casing 11, and is connected to the wiring 14 at the opening edge of the opening 16. Then, the internal electrodes 13 are connected to the wiring 15.

That is to say, in Embodiment 1, the wiring 12 and the internal electrodes 13 are connected by the wiring 14 formed on the outer surface of the casing 11 and the wiring 15 formed on the inner surface of the casing 11. As with the wiring 12, the wiring 14 and the wiring 15 are formed by attaching thin plates or foils of metal onto the surface of the casing 11, or by forming films of a metallic material by vapor deposition, plating, or the like. In Embodiment 1, the connection structure can be realized by such a simple configuration, and therefore it is possible to achieve a further reduction in the manufacturing costs of the sensor cartridge 10.

As shown in FIG. 4, in Embodiment 1, the internal electrodes 13 are formed so as to protrude from the wiring 15, which is located on the ceiling side within the casing 11, toward a bottom surface 18 (i.e., toward the sensor 1). In addition, the internal electrodes 13 are configured to be elastically deformable by pressure. Specifically, the internal electrodes 13 are made of a metallic plate. Further, the internal electrodes 13 are placed so as to protrude in an oblique direction toward the opening 16.

Accordingly, when the sensor 1 is delivered to the opening 16 side and the internal electrodes 13 come into contact with the cover 3 of the sensor 1, the internal electrodes 13 are deformed so as not to interfere with the movement of the sensor 1. Then, when the cover 3 of the sensor 1 has passed under the internal electrodes 13, the internal electrodes 13 return by an elastic force toward the electrodes 5 and 6, and come into contact with the electrodes 5 and 6. Further, as shown in FIG. 4, each of the sensors 1 moves on the bottom surface 18 provided within the casing 11.

As shown in FIGS. 1 and 6, in Embodiment 1, the sensor cartridge 10 further includes a delivery mechanism 20, and the movement of the sensor 1 is effected by the delivery mechanism 20. The delivery mechanism 20 discharges the sensor located at a preset location (the head of the line). In addition, the delivery mechanism 20 causes the sensor that is placed adjacent to the discharged sensor 1, that is, the sensor 1 that is placed next to the leading sensor to be located at the preset location, that is, at the head of the line.

Specifically, the delivery mechanism 20 includes a pushing member 21, a slider 22, a pair of rails 23a and 23b, and a groove 24 provided in the casing 11. Of these, the pushing member 21 is in contact with the sensor 1 located at the tail end of the line, and moves on the bottom surface 18 (see FIG. 4) provided within the casing 11 while pushing that sensor 1. Note that the illustration of the delivery mechanism 20 is omitted in FIG. 4.

The slider 22 is coupled to the pushing member 21. Accordingly, when the user causes the slider 22 to move along the groove 24, the pushing member 21 also moves along with the slider 22. Then, the sensor 1 is pushed by the pushing member 21, and the sensor 1 also moves in conjunction with the slider 22. As a result, the sensor 1 located at the head of the line is pushed to the outside of the casing 11, and is discharged. Then, the sensor 1 placed next to the discharged sensor 1 will be located at the head of the line.

The rails 23a and 23b are provided within the casing 11 so as to extend in the direction in which the sensors are lined up. The slider 22 is sandwiched between the rail 23a and 23b, and can move linearly in the direction of the line. The rail 23a and 23b restrict the movement of the slider 22 and the pushing member 21 in a direction other than the direction of the line. Further, the rails 23a and 23b are in contact with the top surface of the cover 3 of the sensors 1 excluding the sensor 1 located at the preset location (the head of the line), and press the sensor 1 against the bottom surface 18.

With a configuration including such rails 23a and 23b, it is possible to prevent such a situation where movement using the slider 22 becomes unsmooth due to misalignment of the sensors 1 and it is difficult to move the sensors 1. Further, according to Embodiment 1, it is possible, with the delivery mechanism 20, to easily discharge a used sensor 1 and easily set a new sensor 1, thus further improving the convenience for the user.

Although not shown in the example in FIG. 6, it is preferable that the delivery mechanism 20 is additionally provided with a configuration for restricting the movement of the slider 22 in the direction of the line such that the sensors 1 can be delivered one by one. Specifically, it is preferable that the groove 24 is provided with a projection or the like in a position corresponding to the position of the slider 22 at the time when one sensor 1 is discharged and the next sensor 1 is placed at the head.

The configuration of the delivery mechanism 20 is not limited to the example shown in FIG. 6. Another example of the delivery mechanisms 20 is a mechanism in which the casing 11 is provided with a sheet member on a principal surface of which a plurality of sensors 1 can be placed, and the sensors 1 are moved by moving this sheet member.

As shown in FIG. 1, in Embodiment 1, the sensor cartridge 10 includes a wiring pattern 17 on the outer surface of the casing 11, separately from the wiring 12. The wiring pattern 17 functions as an information presentation portion that presents information relating to a plurality of sensors 1 housed in the casing 11. In the example in FIG. 1, the wiring pattern 17 includes wiring 17a, wiring 17b, and wiring 17c, and presents the information relating to the plurality of sensors 1 that are housed. The measuring device 30 recognizes the presented information using the wiring pattern 17.

Here, "information relating to the sensors" includes information indicating a calibration curve suited for a sensor 1. In general, the measuring device 30 includes a plurality of calibration curves in order to increase the measurement accuracy. Then, the measuring device 30 needs to select a calibration curve in accordance with the production lot or the like of the sensor 1. In this case, if each type of wiring pattern is associated in advance with a calibration curve, then the measuring device 30 can select an appropriate calibration curve by detecting the wiring pattern 17.

Specifically, the measuring device 30 includes electrodes 33 as shown in FIG. 4. Although only one electrode 33 is shown in the example in FIG. 4, a plurality of electrodes 33 are actually provided. Then, the measuring device 30 specifies the type of the wiring pattern 17 by detecting the number of the electrodes 33 that were able to come into contact with the wiring constituting the wiring pattern 17, and can select an appropriate calibration curve based on the specified type of the wiring pattern 17. In this case, the measuring device 30 can easily specify an appropriate calibration curve, and therefore it is possible to improve the measurement accuracy and shorten the measurement time.

(Modification 1)

Figure 7:
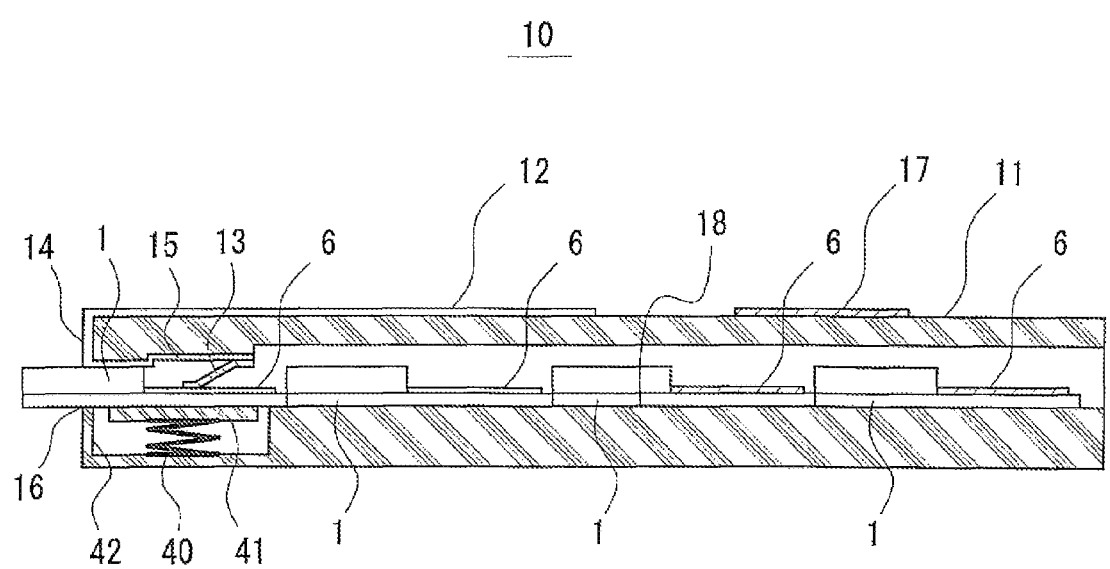
FIG. 7 is a cross-sectional view showing the configuration of another example of the sensor cartridge according to Embodiment 1 of the invention.

Next, Modification 1 of the sensor cartridge 10 according to Embodiment 1 will be described with reference to FIG. 7. FIG. 7 is a cross-sectional view showing the configuration of another example of the sensor cartridge according to Embodiment 1 of the invention.

In the example in FIG. 7, provided within the casing 11 of the sensor cartridge 10 is a pressing member 41 that presses the sensor 1 located at the head such that the sensor electrodes 5 and 6 (in FIG. 7, the sensor electrode 5 is not shown) of the sensor 1 located at the head are pressed against the internal electrodes 13.

Specifically, in the example in FIG. 7, a recess 42 is provided in a region of the bottom surface 18 on the opening 16 side. Further, an elastic body 40 is placed in the recess 42. The elastic body 40 presses the pressing member 41 toward the sensor 1 by its elastic force. Although the elastic body 40 is a coil spring in the example in FIG. 7, the elastic body 40 is not limited thereto and may be a plate spring, a rubber mass, or the like. With the configuration shown in FIG. 7, it is possible to establish a more solid connection between the sensor electrodes 5 and 6 and the internal electrodes 13, thus further improving the connection stability.

(Modification 2)

Figure 8:
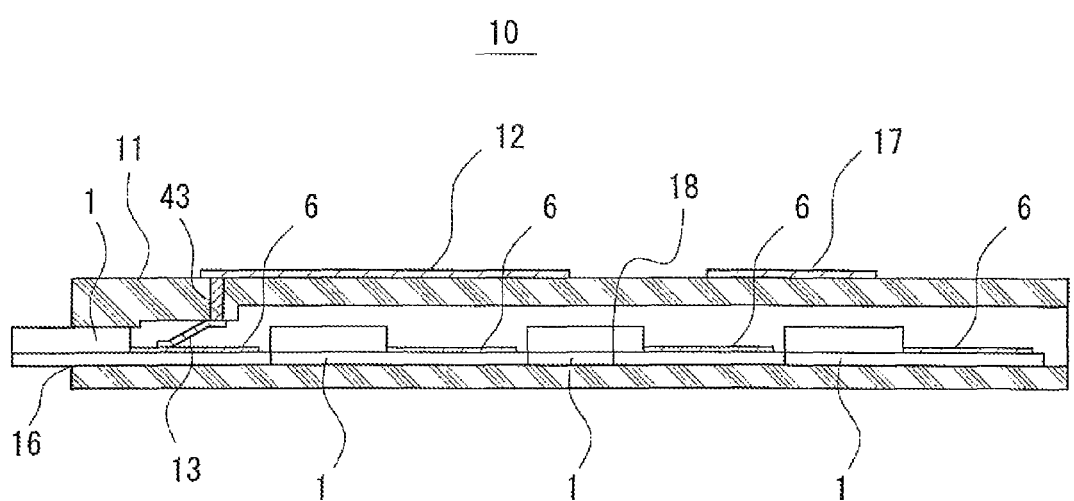
FIG. 8 is a cross-sectional view showing the configuration of another example of the sensor cartridge according to Embodiment 1 of the invention.

Next, Modification 2 of the sensor cartridge 10 according to Embodiment 1 will be described with reference to FIG. 8. FIG. 8 is a cross-sectional view showing the configuration of another example of the sensor cartridge according to Embodiment 1 of the invention.

In the example in FIG. 8, the wiring 12 is connected to the internal electrodes 13 via a conduction path 43. The conduction path 43 is provided so as to penetrate the wall of the casing 11. Specifically, the conduction path 43 can be formed by forming a through-hole in the wall of the casing 11, and filling the through-hole with a conductive material or forming a conductive film on the wall surface of the through-hole. With the configuration shown in FIG. 8, it is possible to reduce the wiring resistance by connecting the wiring 12 and the internal electrodes 13 with a short wiring distance, thus improving the measurement accuracy.

(Modification 3)

Figure 9:
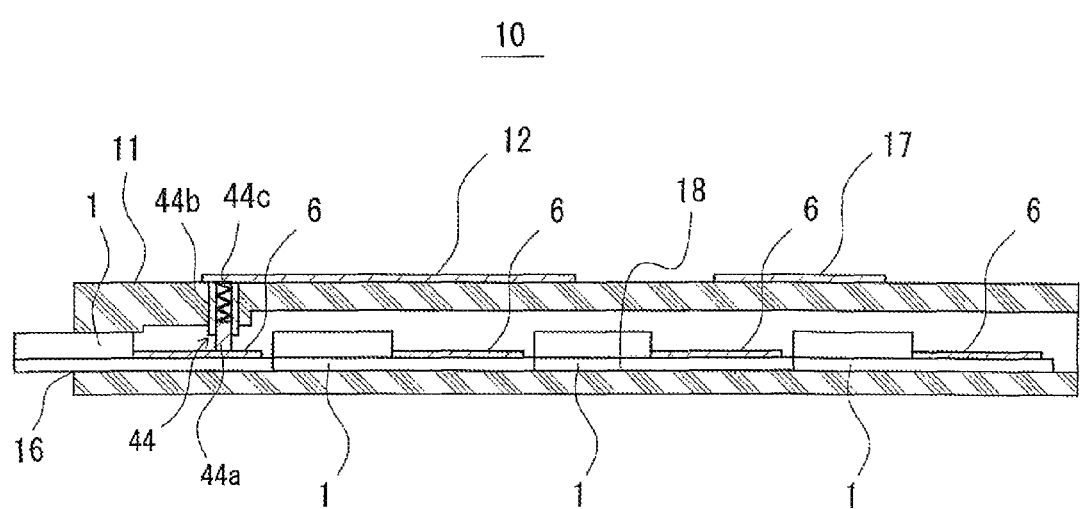
FIG. 9 is a cross-sectional view showing the configuration of another example of the sensor cartridge according to Embodiment 1 of the invention.

Next, Modification 3 of the sensor cartridge 10 according to Embodiment 1 will be described with reference to FIG. 9. FIG. 9 is a cross-sectional view showing the configuration of another example of the sensor cartridge according to Embodiment 1 of the invention.

In the example in FIG. 9, an electrode 44 for being connected to the sensor electrode 6 of the sensor 1 located at the head is provided within the casing 11. The electrode 44 includes a conductive pipe member 44b penetrating through the wall of the casing 11, a conductive pin member 44a, and an elastic body 44c. Of these, the pipe member 44b is connected to the wiring 12.

The pin member 44a is formed so as to be slidable along the inner wall of the pipe member 44b, and is placed within the pipe member 44b. The elastic body 44c is placed within the pipe member 44b such that the pin member 44a is pressed toward the sensor electrode 6 by the elastic force of the elastic body 44c. Further, although not shown in FIG. 9, a pin member 44a, a pipe member 44b, an elastic body 44c, and wiring 12 corresponding to the sensor electrode 5 are also provided.

With this configuration, in the example in FIG. 9, the sensor electrodes 5 and 6 of the sensor 1 located at the head are electrically connected to the wiring 12 via the pin members 44a and the pipe members 44b. Since the pin members 44a are pressed against the sensor electrodes 5 and 6 by the elastic force of the elastic bodies 44c, the sensor electrodes 5 and 6 are electrically connected to the wiring 12 via the pin members 44a and the pipe members 44b in a reliable manner.

At the time of replacing the sensors 1, the pin member 44a is pushed upward by a lever (not shown in FIG. 9) or the like that is connected to the pin member 44a. Although the elastic body 44c is a coil spring in the example in FIG. 9, the elastic body 44c is not limited thereto. The elastic body 44c may be a plate spring, a rubber mass, or the like.

A measurement method according to Embodiment 1 can be realized using the sensor cartridge 10 and the measuring device 30 shown in FIGS. 1 to 9. Specifically, first, the sensor cartridge 10 is attached to the measuring device 30, and a sample is introduced from the inlet 4 of the sensor 1 located at the head in the sensor cartridge.

Next, from the electrode 32 provided within the device body 31 of the measuring device 30, a voltage is applied between the sensor electrode 5 and the sensor electrode 6 of the sensor 1 via the wiring 12, the wiring 14, the wiring 15, and the internal electrodes 13 (or the electrodes 44) of the sensor cartridge 10, and data measurement is carried out. Then, the living body numerical information is calculated from the measured data. Specifically, when the measuring device 30 is a glucose meter, the measured current values are fitted to a calibration curve to calculate the blood glucose level.

Thereafter, the sensor 1 used for calculation of the living body numerical information is discharged, and the sensor 1 placed next to the discharged sensor 1 is located at the head of the line. In Embodiment 1, prior to the first measurement using the sensor 1, the measuring device 30 may acquire information relating to an appropriate calibration curve based on the wiring pattern 17 provided on the outer surface of the casing 11, and select a calibration curve based on this information.

As described above, according to Embodiment 1, unlike with the conventional technology, it is possible to reduce the manufacturing costs by simplifying the structure of the measuring device 30. Furthermore, it is not necessary to perform the positioning of the electrodes each time measurement is carried out as with the conventional technology, and therefore it is possible to carry out stable measurements. Furthermore, since the sensor cartridge 10 that supplies a plurality of sensors 1 is held by the device body 31 of the measuring device 30, the handleability for the user is improved.

Furthermore, according to Embodiment 1, it is not necessary to set the sensors 1 in the measuring device 30 one by one, and therefore the size reduction of the sensors 1 can be easily realized. In addition, the wiring 12 for connecting to the outside of the sensor cartridge 10 will not be influenced by the sensor size and the contact area thereof can be set large, and therefore it is possible to facilitate connection between the sensor cartridge 10 and the electrodes of the measuring device 30.

Although in Embodiment 1 described above, an example is shown in which a plurality of sensors 1 are arranged in a line within the casing 11 of the sensor cartridge 10 and measurement is carried out using the sensor located at the head of the line, the present invention is not limited to this example.

For example, the casing 11 may be configured such that a plurality of sensors 1 can be arranged in a plurality of lines. In this case, the opening 16 of the casing 11 exposes the sample inlet 4 of the sensor 1 located at the head of any one of the lines. Then, the internal electrodes 13 are placed so as to come into contact with the sensor electrodes 5 and 6 of the sensor 1 located at the head of that line.

Embodiment 2

Figure 10:
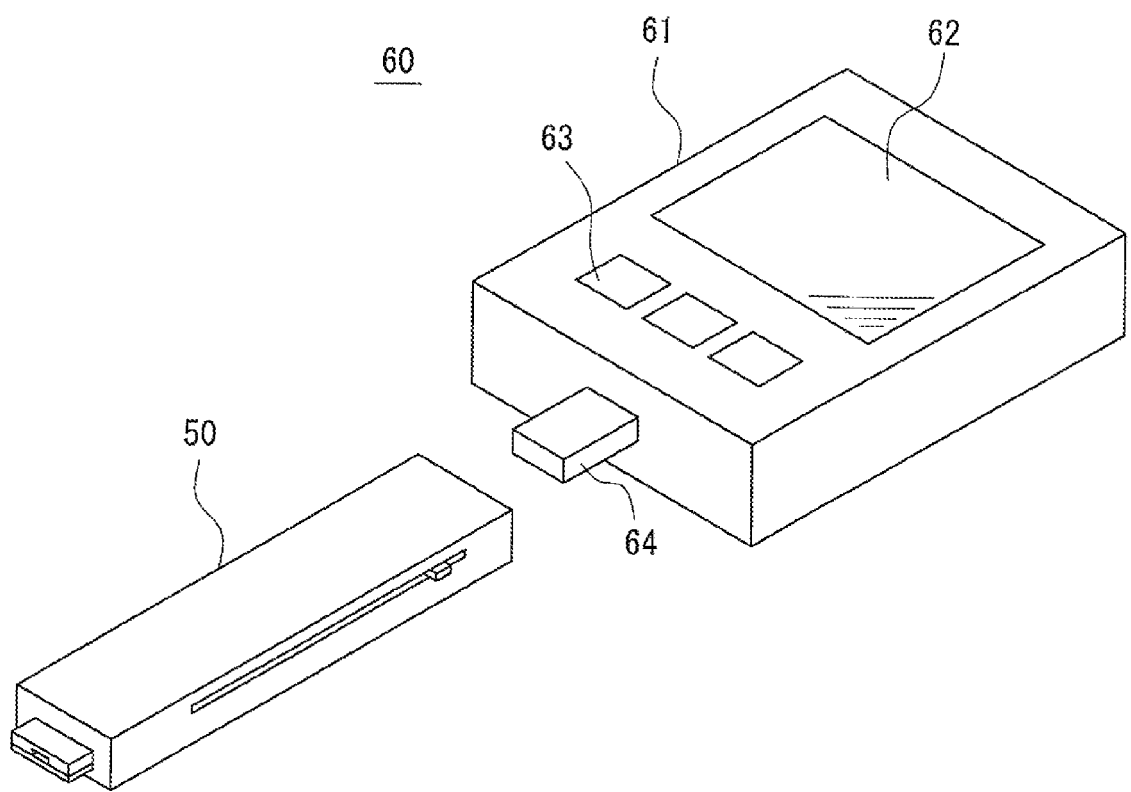
FIG. 10 is a perspective view showing the appearance of a sensor cartridge and a measuring device according to Embodiment 2 of the invention.
Figure 11:
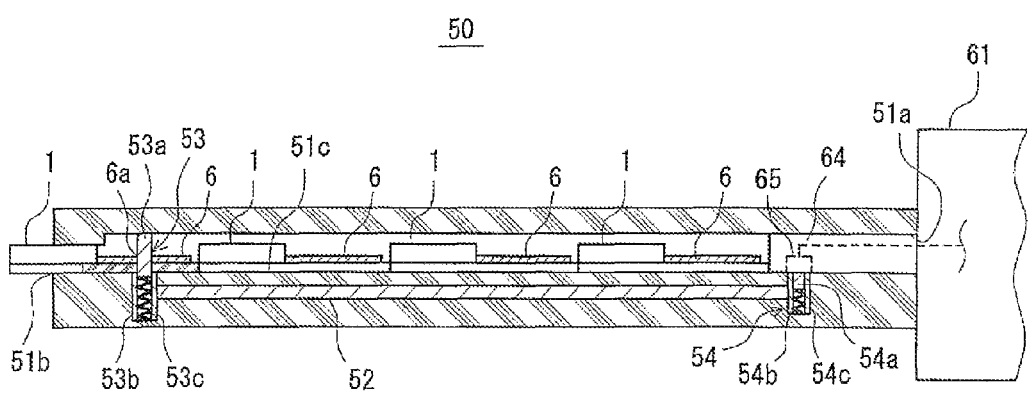
FIG. 11 is a cross-sectional view showing the configuration of the sensor cartridge according to Embodiment 2 of the invention.

Next, a sensor cartridge 50 and a measuring device 60 according to Embodiment 2 of the present invention will be described with reference to FIGS. 10 and 11. FIG. 10 is a perspective view showing the appearance of a sensor cartridge and a measuring device according to Embodiment 2 of the invention. FIG. 11 is a cross-sectional view showing the configuration of the sensor cartridge according to Embodiment 2 of the invention.

As shown in FIG. 10, the measuring device 60 includes the sensor cartridge 50 and a device body 61 that holds the sensor cartridge 50. In Embodiment 2, the device body 61 includes a connector 64 that can be inserted into a casing 51 of the sensor cartridge 50, and electrical connection to the sensor cartridge 50 and holding of the sensor cartridge 50 are carried out with the connector 64. In the following, the sensor cartridge 50 and the measuring device 60 will be described, focusing on dissimilarities to Embodiment 1. In FIG. 10, reference numeral 62 denotes a display screen, and reference numeral 63 denotes an operation button.

As shown in FIG. 11, the casing 51 of the sensor cartridge 50 is configured such that a plurality of sensors 1 can be arranged within the casing 51, as with the sensor cartridge 10 (see FIGS. 1, 3, and 4) according to Embodiment 1, but the rest of the configuration is different from that of Embodiment 1. Each of the sensors 1 includes a through-hole 6a penetrating the sensor substrate 2 (see FIGS. 2A and 2B) and the sensor electrode 6, and a through-hole penetrating the sensor substrate 2 and the sensor electrode 5. Note that the sensor electrode 5 and a through-hole penetrating therethrough are omitted in FIG. 11. In addition, the sensor substrate 2 and the sensor electrode 6 are partly shown in cross section only for the sensor 1 located at the head.

As shown in FIG. 11, the casing 51 is formed such that the connector 64 of the device body 61 can be inserted into the casing 51. Additionally, an opening 51a into which the connector 64 can be inserted is provided in the casing 51 on the side when the tail end sensor 1 is located. The connector 64 is provided with an electrode 65. Reference numeral 51*b* denotes an opening for exposing the sensor 1 located at the head, and reference numeral 51*c* denotes the bottom surface within the casing 51.

As shown in FIG. 11, unlike the sensor cartridge 10 in Embodiment 1, the connection structure is configured such that no wiring is exposed to the outside of the casing 51. In Embodiment 2, the connection structure includes internal wiring 52 provided within the casing 51, an electrode 53 for being connected to the sensor electrode 6, and an electrode 54 for being connected to the electrode 65 of the connector 64.

Specifically, in the example in FIG. 11, the internal wiring 52 is embedded in the casing 51 below the sensor 1. Further, the electrode 53 for being connected to the sensor electrode 6 includes a conductive pin member 53*a*, a conductive pipe member 53*b* for being connected to the internal wiring 52, and an elastic body 53*c*.

Of these, the pipe member 53*b* is embedded in the bottom surface 51*c* in the normal direction of the bottom surface 51*c* in a position facing the through-hole 6*a* of the sensor 1 at the head. The pin member 53*a* is formed so as to be slidable along the inner wall of the pipe member 53*b*, and is placed within the pipe member 53*b*. The elastic body 53*c* is placed within the pipe member 53*b* such that the pin member 53*a* is pressed toward the sensor electrode 6 by the elastic force of the elastic body 53*c*.

Also, the electrode 54 for being connected to the electrode 65 of the device body 61 includes a conductive pin member 54*a*, a conductive pipe member 54*b* for being connected to the internal wiring 52, and an elastic body 54*c*. The pipe member 54*b* is embedded in the bottom surface 51*c* in the normal direction of the bottom surface 51*c* in a position facing the electrode 65 of the connector 64. The pin member 54*a* is formed so as to be slidable along the inner wall of the pipe member 54*b*, and is placed within the pipe member 54*b*. The elastic body 54*c* is placed within the pipe member 54*b* such that the pin member 54*a* is pressed toward the electrode 65 of the connector 64 by the elastic force of the elastic body 54*c*.

Accordingly, when the sensor 1 is placed at a predetermined position, the pin member 53*a* of the electrode 53 penetrates through the through-hole 6*a* of the sensor 1, and is connected to the sensor electrode 6 in a reliable manner. Then, the sensor electrode 6 is electrically connected to the internal wiring 52 via the pin member 53*a* and the pipe member 53*b*.

When the connector 64 is inserted into the opening 51*a* of the casing 51, the pin member 54*a* of the electrode 54 comes into contact with the electrode 65 provided in the connector 64. At that time, since the pin member 54*a* is pressed by the elastic body 54*c*, the electrical connection between the pin member 54*a* and the electrode 65 is ensured. As a result, the internal wiring 52 is electrically connected to the electrode 65 via the pipe member 54*b* and the pin member 54*a*.

As described above, according to Embodiment 2, it is possible, with the sensor cartridge 50, to electrically connect the sensor electrode 6 and the electrode 65 of the device body 61 in a simple and reliable manner. Although not shown in FIG. 11, the sensor cartridge 50 is also provided with an electrode 53, internal wiring 52, and an electrode 54 corresponding to the sensor electrode 5. Accordingly, it is also possible, with the sensor cartridge 50, to connect the sensor electrode 5 and the electrode 65 of the device body 61 in a simple and reliable manner.

In addition to the above-described effects, all the effects described in Embodiment 1 can also be achieved by using Embodiment 2. That is, it is possible, with Embodiment 2, to simplify the structure of the measuring device 60, thus reducing the manufacturing costs. Further, since it is not necessary to perform the positioning of the electrodes each time measurement is carried out as with the conventional technology, it is possible to perform stable measurements. Moreover, since the sensor cartridge 50 is held by the device body 61 of the measuring device 60, the handleability for the user is improved. Additionally, since the contact area of the electrode for connecting to the outside of the sensor cartridge 50 can be set independent of the size of the sensor 1, it is possible to easily connect the sensor cartridge 50 and the electrode 65 of the device body 61 even if the sensor 1 is miniaturized.

Although not shown in FIG. 11, the casing 51 is provided with a lever for pushing the pin member 53*a* downward and a lever for pushing the pin member 54*a* downward. The former lever is used at the time of replacing the sensors 1. The latter lever is used at the time of inserting the connector 64. Although each of the elastic bodies 53*c* and 54*c* is a coil spring in the example in FIG. 11, the elastic bodies 53*c* and 54*c* are not limited thereto. The elastic bodies 53*c* and 54*c* may be a plate spring, a rubber mass, or the like. Furthermore, in the example in FIG. 11, a hole whose inner wall is covered with a conductive material may be provided in the casing 51, in place of the pipe members 53*b* and 54*b*.

(Modification 1)

Figure 12:
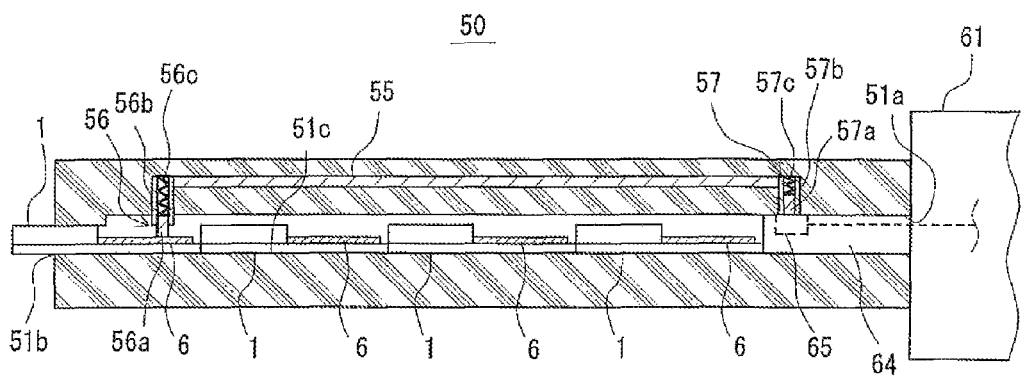
FIG. 12 is a cross-sectional view showing the configuration of another example of the sensor cartridge according to Embodiment 2 of the invention.

Next, Modification 1 of the sensor cartridge 50 according to Embodiment 2 of the present invention will be described with reference to FIG. 12. FIG. 12 is a cross-sectional view showing the configuration of another example of the sensor cartridge according to Embodiment 2 of the invention.

In the example in FIG. 12, unlike the example in FIG. 11, the electrode 65 for being connected to the sensor cartridge 50 of the device body 61 is provided on the top surface side of the connector 64. In addition, the configuration of the connection structure in the sensor cartridge 50 is different from that of the example in FIG. 11.

In the example in FIG. 12 as well, the connection structure includes internal wiring 55 provided within the casing 51, an electrode 56 for being connected to the sensor electrode 6, and an electrode 57 for being connected to the electrode 65 of the connector 64, but they are provided above the sensor 1. In other words, the internal wiring 55 is embedded in the casing 51 above the sensor 1.

Further, the electrode 56 for being connected to the sensor electrode 6 includes a pin member 56*a*, a pipe member 56*b*, and an elastic body 56*c* as with the electrodes 53 and 54 shown in FIG. 11, but they are provided above the sensor electrode 6. Specifically, the pipe member 56*b* is embedded above the sensor electrode 6 in a position facing the sensor electrode 6. Further, the pin member 56*a* is placed within the pipe member 56*b*, and is pressed by the elastic body 56*c* toward the electrode 6 from above.

Furthermore, the electrode 57 for being connected to the electrode 65 of the connector 64 as well includes a pin member 57*a*, a pipe member 57*b*, and an elastic body 57*c* as with the electrodes 53 and 54 shown in FIG. 11. However, they are also provided above the connector 64. Specifically, the pipe member 57*b* is embedded above the electrode 65 of the connector 64 in a position facing the electrode 65. Further, the pin member 57*a* is placed within the pipe member 57*b*, and is pressed by the elastic body 57*c* toward the electrode 65 of the connector 64 from above.

Accordingly, when the sensor 1 is placed at a predetermined position, the pin member 56*a* is electrically connected to the sensor electrode 6 in a reliable manner. When the connector 64 is inserted into the opening 51*a* of the casing 51, the pin member 57*a* is connected to the electrode 65 in a reliable manner. Also, the pipe member 56*b* and the pipe member 57*b* are electrically connected by the internal wiring 55.

Accordingly, in the example in FIG. 12 as well, it is possible to electrically connect the sensor electrode 6 and the electrode 65 of the device body 61 in a simple and reliable manner. Although not shown in FIG. 12, an electrode 56, internal wiring 55, and an electrode 57 corresponding to the sensor electrode 5 are also provided, and therefore it is also possible to electrically connect the sensor electrode 5 and the electrode 65 of the device body 61 in a simple and reliable manner.

Although not shown in the example in FIG. 12, the casing 51 is provided with a lever for pushing the pin member 56*a* upward and a lever for pushing the pin member 57*a* upward. The former lever is used at the time of replacing the sensors 1. The latter lever is used at the time of inserting the connector 64. In the example in FIG. 12 as well, each of the elastic bodies 56*c* and 57*c* may be a plate spring, a rubber mass, or the like, other than a coil spring. Furthermore, in the example in FIG. 12 as well, a hole whose inner wall is covered with a conductive material may be provided in the casing 51, in place of the pipe members 56*b* and 57*b*.

(Modification 2)

Figure 13:
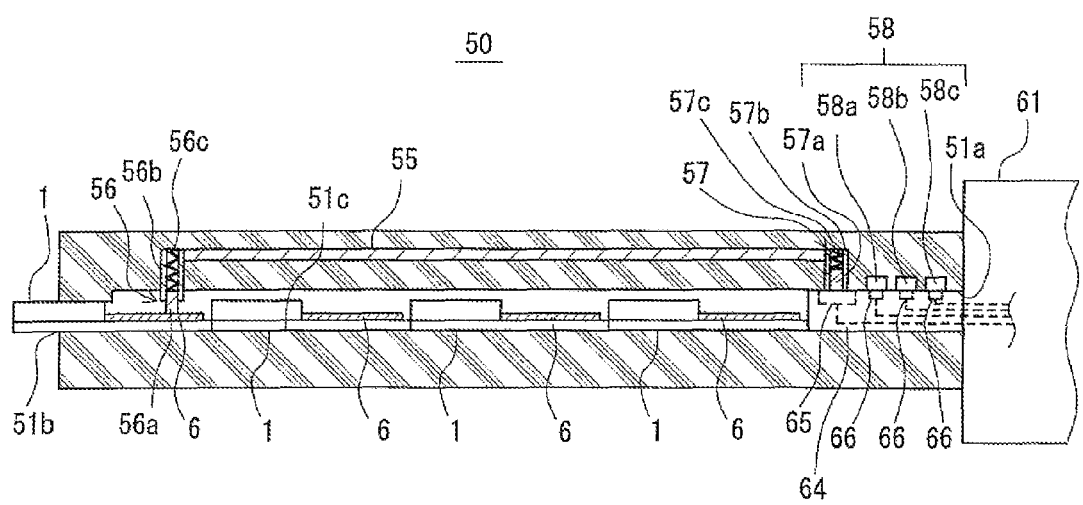
FIG. 13 is a cross-sectional view showing the configuration of another example of the sensor cartridge according to Embodiment 2 of the invention.

Next, Modification 2 of the sensor cartridge 50 according to Embodiment 2 will be described with reference to FIG. 13. FIG. 13 is a cross-sectional view showing the configuration of another example of the sensor cartridge according to Embodiment 2 of the invention.

In the example in FIG. 13, a wiring pattern 58 is provided within the casing 51 constituting the sensor cartridge 50. The rest of the configuration is the same as that of Modification 1 shown in FIG. 12. In the following, dissimilarities to Modification 1 will be described.

The wiring pattern 58 has the same function as that of the wiring pattern 17 shown in FIG. 1 in Embodiment 1. As with the wiring pattern 17, the wiring pattern 58 functions as an information presentation portion that presents information relating to a plurality of sensors 1 housed in the casing 51. In the example in FIG. 13, the wiring pattern 58 includes wiring 58*a*, wiring 58*b*, and wiring 58*c*, and information relating to the plurality of sensors 1 that are housed is presented by using such wiring.

The wiring 58*a*, the wiring 58*b*, and the wiring 58*c* constituting the wiring pattern 58 are placed at positions that are located above the connector 64 and adjacent to the electrode 57, and they are in contact with electrodes 66 provided in the connector 64. The measuring device 60 recognizes "information relating to the sensors" presented by the wiring pattern 58 by using the electrodes 66. Examples of the "information relating to the sensors" include information indicating a calibration curve suited for the sensors 1, as described also in Embodiment 1.

In this way, according to Modification 2, the measuring device 60 can easily specify an appropriate calibration curve. Accordingly, with Modification 2, it is possible to improve the measurement accuracy and reduce the measurement time even further.

(Modification 3)

Figure 14:
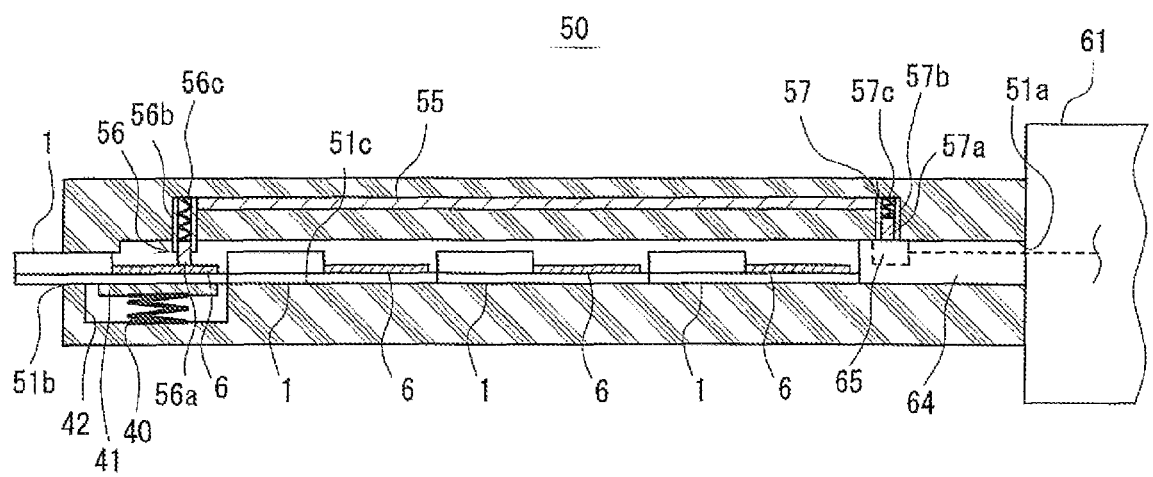
FIG. 14 is a cross-sectional view showing the configuration of another example of the sensor cartridge according to Embodiment 2 of the invention.

Next, Modification 3 of the sensor cartridge 50 according to Embodiment 2 will be described with reference to FIG. 14. FIG. 14 is a cross-sectional view showing the configuration of another example of the sensor cartridge according to Embodiment 2 of the invention.

In the example in FIG. 14, as with Modification 1 described with reference to FIG. 7 in Embodiment 1, a pressing member 41 for pressing the sensor 1 located at the head is provided within the casing 51 constituting the sensor cartridge 50. The rest of the configuration is the same as that of Modification 1 shown in FIG. 12.

That is, as shown in FIG. 14, a recess 42 is provided in a region of the bottom surface 51*c* on the opening 51*b* side. Further, the elastic body 40 is placed in the recess 42. The elastic body 40 presses the pressing member 41 toward the sensor 1 by its elastic force. Accordingly, with the example in FIG. 14 as well, it is possible to establish a more solid connection between the sensor electrodes 5 and 6 (in FIG. 14, the sensor electrode 5 is not shown) and the electrodes 56, thus improving the connection stability, as with Modification 1 shown in FIG. 7 according to Embodiment 1.

(Modification 4)

Figure 15:
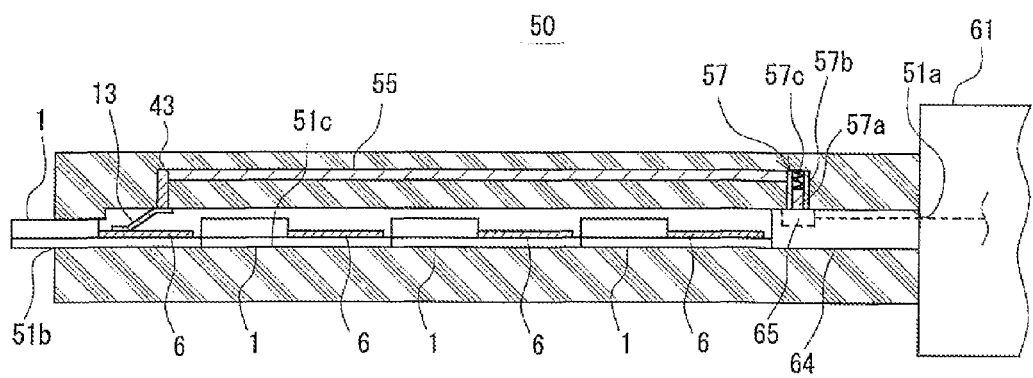
FIG. 15 is a cross-sectional view showing the configuration of another example of the sensor cartridge according to Embodiment 2 of the invention.

Next, Modification 4 of the sensor cartridge 50 according to Embodiment 2 will be described with reference to FIG. 15. FIG. 15 is a cross-sectional view showing the configuration of another example of the sensor cartridge according to Embodiment 2 of the invention.

In the example in FIG. 15, internal electrodes 13 are provided as the electrodes for being connected to the sensor electrodes 5 and 6, as with Modification 2 described with reference to FIG. 8 in Embodiment 1. Further, the internal electrodes 13 are connected to internal wiring 55 via a conduction path 43. The rest of the configuration is the same as that of Modification 1 shown in FIG. 12.

Since the internal electrodes 13 in the example shown in FIG. 15 are configured to be elastically deformable as described in Embodiment 1, the internal electrodes 13 and the sensor electrodes 5 and 6 (in FIG. 15, the sensor electrode 5 is not shown) are electrically connected in a reliable manner. Further, when the sensor 1 is delivered to the opening 51*b* side and the internal electrodes 13 come into contact with the sensor 1, the internal electrodes 13 are deformed so as not to interfere with the movement of the sensor 1. Thereafter, the internal electrodes 13 return by an elastic force toward the electrodes 5 and 6, and come into contact with the electrodes 5 and 6.

Embodiment 3

Figure 16:
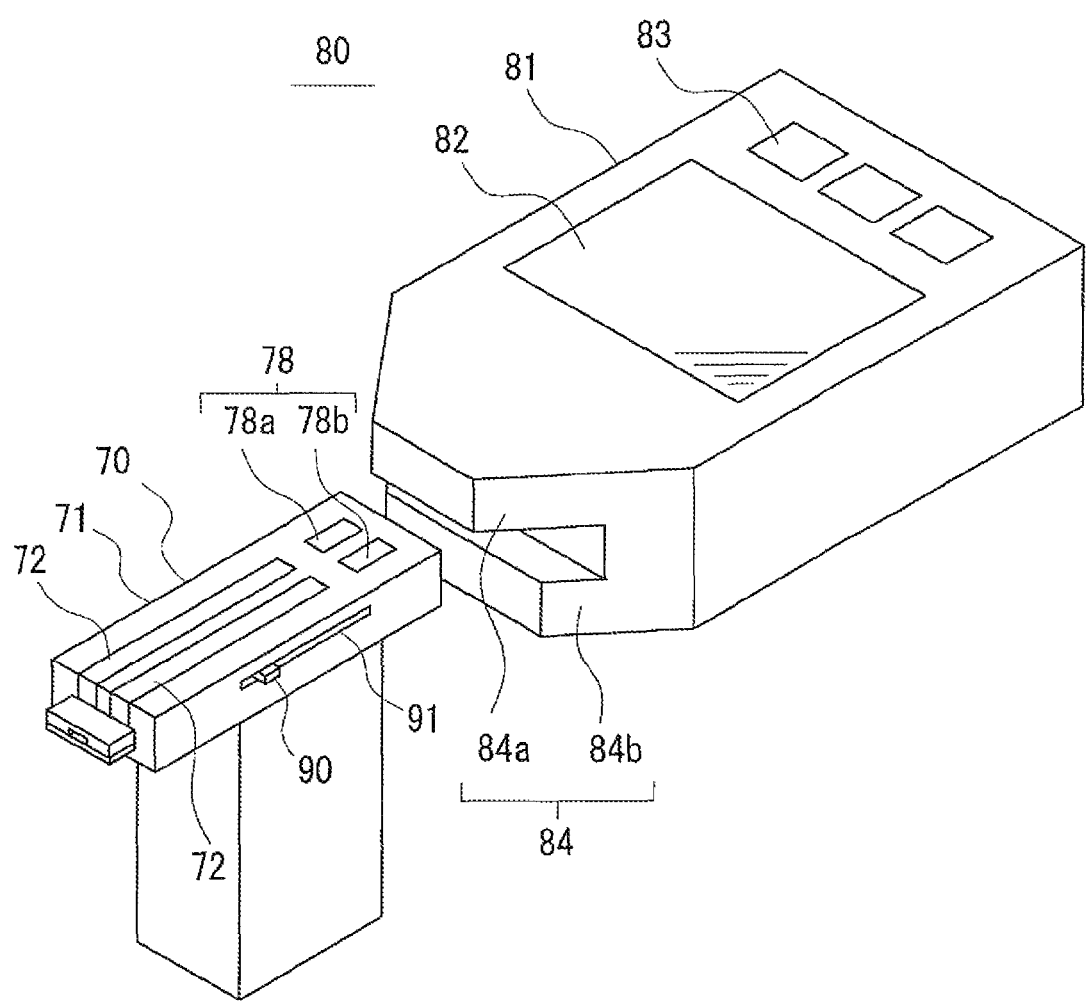
FIG. 16 is a perspective view showing the appearance of a sensor cartridge and a measuring device according to Embodiment 3 of the invention.
Figure 17:
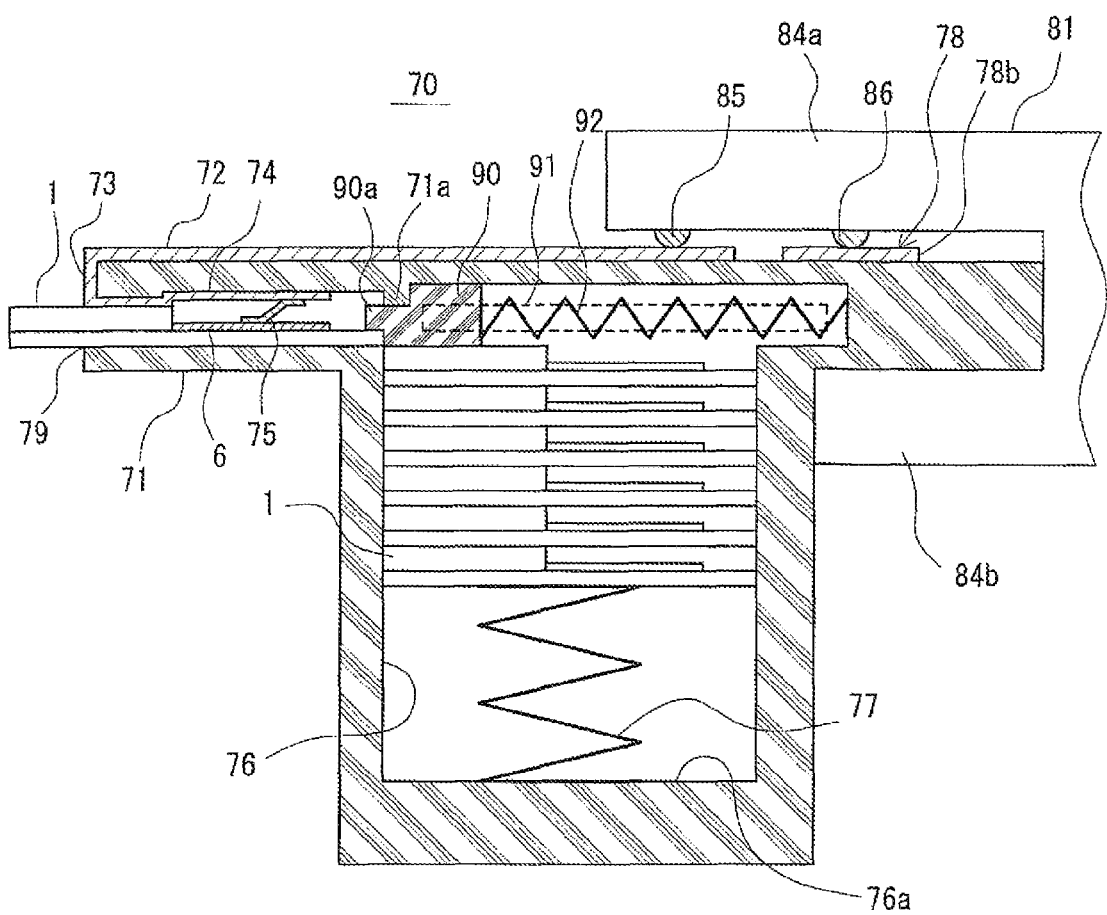
FIG. 17 is a cross-sectional view showing the configuration of the sensor cartridge according to Embodiment 3 of the invention.

Next, a sensor cartridge 70 and a measuring device 80 according to Embodiment 3 of the invention will be described with reference to FIGS. 16 and 17. FIG. 16 is a perspective view showing the appearance of a sensor cartridge and a measuring device according to Embodiment 3 of the invention. FIG. 17 is a cross-sectional view showing the configuration of the sensor cartridge according to Embodiment 3 of the invention.

As shown in FIG. 16, the measuring device 80 includes a sensor cartridge 70, and a device body 81 that holds the sensor cartridge 70, as with the measuring devices described in Embodiments 1 and 2. However, unlike Embodiments 1 and 2, a casing 71 of the sensor cartridge 70 in Embodiment 3 is configured such that a plurality of sensors 1 can be arranged in a stacking direction.

Specifically, as shown in FIG. 17, a space 76 in which a plurality of sensors 1 stacked in the thickness direction can be housed is provided within the casing 71. In addition, an elastic body 77 is provided between a bottom surface 76*a* of the space 76 and the stacked sensors 1, and the sensors 1 are constantly pressed upward by the elastic body 77.

Provided above the stacked sensors 1 is a slider 90 for delivering the sensors 1 one by one toward an opening 79 provided in the casing 71. The slider 90 moves in a direction (hereinafter, referred to as "horizontal direction") perpendicular to the stacking direction using a groove 91 (see FIG.

16) as its guide. Further, an elastic body 92 is provided on the side of the slider 90 that is opposite to the opening 79 side, and the slider 90 is constantly pressed toward the opening 79 by the elastic body 92.

Accordingly, when the user pulls the slider 90 of the sensor cartridge 70 away from the opening 79, the sensor 1 located at the top is pushed by the elastic body 77 due to the absence of an obstacle above that sensor, and is moved to the space between the opening 79 and the slider 90. At that time, the sensor 1 is positioned by the tip of a projection 71a provided within the casing 71 and the bottom of a projection 90a provided in the slider 90.

Then, when the user relaxes the force pulling the slider 90, the sensor 1 is moved along with the slider 90 toward the opening 79 by the elastic force of the elastic body 92. At that time, if a sensor 1 is already placed on the opening 79 side, the placed sensor 1 is pushed by the next sensor 1 that has been moved, and is discharged to the outside of the sensor cartridge 70.

Since the movement of the slider 90 toward the opening 79 is restricted by the projection 71a provided within the casing 71, the sensor 1 that has been moved by the slider 90 is positioned at a location most suitable for the sample introduction.

In Embodiment 3, the connection structure is configured in the same manner as the connection structure shown in FIGS. 1 and 4 in Embodiment 1. That is, the connection structure includes wiring 72 provided on the outer surface of the casing 71, internal electrodes 75 (see FIG. 17) provided within the casing 71, and wiring 73 and 74 for connecting the wiring 72 and the internal electrodes 75. Further, the internal electrodes 75 are configured in the same manner as the internal electrodes 13 shown in FIG. 4, and are placed so as to come into contact with the sensor electrodes 5 and 6 (in FIG. 17, the sensor electrode 5 is not shown) of the sensor 1 located at the top.

The casing 71 is also provided with a wiring pattern 78 that is similar to the wiring pattern 17 shown in FIG. 1. The wiring pattern 78 includes wiring 78a and wiring 78b, and functions as an information presentation portion that presents information relating to the plurality of sensors 1 that are housed in the casing 71.

In this way, the connection structure in Embodiment 3 is similar to that in Embodiment 1. However, the device body 81 of the measuring device 80 in Embodiment 3 holds the sensor cartridge 70 by a configuration different from that in Embodiment 1.

As shown in FIGS. 16 and 17, in Embodiment 3, the device body 81 holds the sensor cartridge 70 by sandwiching an end of the sensor cartridge 70. Specifically, the device body 81 includes a grasping portion 84 for sandwiching an end of the sensor cartridge 70. The grasping portion 84 includes a first grasper 84a that comes into contact with the sensor cartridge 70 from the wiring 72 side and a second grasper 84b that comes into contact with the sensor cartridge 70 from the opposite side.

As shown in FIG. 17, an electrode 85 that comes into contact with the wiring 72 and an electrode 86 that comes into contact with the wiring of the wiring pattern 78 are provided on the inner surface of the first grasper 84a. Accordingly, using the device body 81 makes it possible to establish electrical connection between the sensor cartridge 70 and the device body 81 by simply fitting an end of the sensor cartridge 70 into the grasping portion 84. As with the measuring device 30 described in Embodiment 1, the measuring device 80 performs measurement via the electrode 85, and selects a calibration curve via the electrode 86.

As described above, according to Embodiment 3, it is possible, with the sensor cartridge 70, to electrically connect the sensor electrode 6 and the electrode 85 of the device body 81 in a simple and reliable manner. Although not shown in FIG. 17, the sensor cartridge 70 is also provided with a connection structure corresponding to the sensor electrode 5. Accordingly, it is also possible, with the sensor cartridge 70, to connect the sensor electrode 5 and the electrode 85 of the device body 81 in a simple and reliable manner.

In addition to the above-described effects, all the effects described in Embodiment 1 can be achieved also by using Embodiment 3. In other words, with Embodiment 3, it is possible to simplify the structure of the measuring device 80 and reduce the manufacturing costs. Furthermore, since it is not necessary to perform the positioning of the electrodes each time measurement is carried out as in the conventional technology, it is possible to perform stable measurements. Furthermore, since the sensor cartridge 70 is held by the device body 81 of the measuring device 80, the handleability for the user is improved. In addition, since the contact area of the wiring 72 for connecting to the outside of the sensor cartridge 70 can be set independent of the size of the sensor 1, it is possible to easily connect the sensor cartridge 70 and the electrode 85 of the device body 81 even if the sensor 1 is miniaturized.

Although the casing 71 of the sensor cartridge 70 is configured to allow a sample to be introduced to the sensor located at the top in Embodiment 3, the configuration is not limited thereto and the casing 71 may be configured to allow a sample to be introduced to the sensor 1 located at the bottom. In this case, the internal electrodes 75 come into contact with the sensor electrodes 5 and 6 of the sensor 1 located at the bottom. In Embodiment 3, "stacking direction" refers to a direction that coincides with the thickness direction of the substrate 2 constituting the sensor 1 (see FIGS. 2A and 2B).

Furthermore, although the connection structure of the sensor cartridge 70 includes the wiring 72 and 73 provided on the outer surface of the casing 71 and the wiring 74 provided on the inner surface of the casing 71 in the example shown in FIGS. 16 and 17, the connection structure in Embodiment 3 is not limited thereto. For example, the connection structure of the sensor cartridge 70 may be configured such that the wiring is embedded within the casing 71 and is not exposed to the outside of the casing 71, as with the connection structures shown in FIGS. 11 to 15 in Embodiment 2.

In the above case, a connector that can be inserted into the casing may be provided at a location between the first grasper 84a and the second grasper 84b in the device body 81. For example, the connector 64 shown in FIGS. 10 and 11 can be used as the connector. The device body shown in FIGS. 16 and 17 can be used as the device body 81 as long as an electrode connected to the wiring embedded within the casing 71 is provided on the outside of the casing 71.

Although the sensor 1 shown in FIGS. 2A and 2B is used as the sensor in Embodiments 1 to 3 described above, the sensor is not limited thereto. Another example of the sensor is a sensor whose sample inlet is provided on top of the sensor. In the case of using such a sensor, the sensor is placed in the casing of the sensor cartridge without part of the sensor being exposed. In that case, for example, an opening is provided in the top surface of the casing such that a sample can be dropped down to the sample inlet from above.

Although the present invention has been described with reference to embodiments, the invention is not limited to the above-described embodiments. Various modifications that can be understood by a person skilled in the art may be made to the configuration and the details of the present invention within the scope of the invention.

According to the present invention, it is possible to prevent the structure of the measuring device from becoming complex and suppress a reduction in stability of the measurement, while improving the handleability of sensors such as biosensors. The present invention is useful in the fields of sensor cartridges for supplying sensors such as biosensors, and of measuring devices using such sensor cartridges.

What is claimed is:

1. A sensor cartridge for supplying a sensor, comprising:
a casing within which a plurality of sensors are arranged and to allow a sample to be introduced to a sensor located at a preset location within the casing; each of the plurality of sensors includes a sample inlet and a sensor electrode; the plurality of sensors are arranged in a line, and the preset location is at a head of the line; each of the sample inlet of each of the plurality of sensors is facing the head of the line; the casing is configured to allow a sample to be introduced to the sample inlet of the sensor positioned at the head of the line;
a connection structure including internal wiring embedded on the casing to electrically connect the sensor electrode of the sensor located at the head of the line to an external device, and
an information presentation portion adapted to present information relating to the plurality of sensors housed within the casing,
wherein the casing is adapted to be held by the external device when the external device and the sensor electrode of the sensor located at the preset location at the head of the line are electrically connected via the connection structure,
wherein the connection structure is provided within the casing so as not to be exposed to the outside of the casing.

2. The sensor cartridge according to claim 1, wherein a member that presses the sensor located at the preset location is provided within the casing such that the sensor electrode of the sensor located at the preset location is pressed against part of the connection structure.

3. The sensor cartridge according to claim 1, wherein the connection structure comprises a conduction path penetrating through a wall of the casing, and is connected via the conduction path to the sensor electrode of the sensor located at the preset location.

4. The sensor cartridge according to claim 1, wherein the connection structure comprises, within the casing, an electrode that comes into contact with the sensor electrode of the sensor located at the preset location, and an electrode for being connected to the device.

5. The sensor cartridge according to claim 4, wherein one or both of the electrode that comes into contact with the sensor electrode of the sensor located at the preset location and the electrode for being connected to the device are configured to be elastically deformable by pressure.

6. The sensor cartridge according to claim 1,
wherein the sensor cartridge further comprises a delivery mechanism, and
the delivery mechanism discharges the sensor located at the preset location, and causes a sensor placed adjacent to the discharged sensor to be located at the preset location.

7. The sensor cartridge according to claim 6,
wherein the casing comprises a sheet member on a principal surface of which the plurality of sensors can be placed, and
the delivery mechanism causes the sensor placed adjacent to the discharged sensor to be located at the preset location by moving the sheet member.

8. The sensor cartridge according to claim 1, wherein the casing is formed such that at least part of the casing is housed within the device when the device and the sensor electrode of the sensor located at the preset location are electrically connected via the connection structure.

9. The sensor cartridge according to claim 1, wherein the casing comprises an opening that allows the sample to be introduced to the sensor located at the preset location.

10. A measuring device for measuring living body numerical information by using a sensor, comprising:
a sensor cartridge to house and supply the sensor; and a device body configured to hold the sensor cartridge,
wherein the sensor cartridge includes:
a casing within which a plurality of sensors are arranged in a line, each of the plurality of sensors includes a sample inlet and a sensor electrode; the preset location is at a head of the line; each of the sample inlet of each of the plurality of sensors is facing the head of the line;
the casing is configured to allow a sample to be introduced to a sensor located at a preset location at the head of the line; and
a connection structure including internal wiring embedded on the casing to electrically connects the device body and the sensor electrode of the sensor located at the preset location at the head of the line,
an information presentation portion configured to present information relating to the plurality of sensors housed within the casing,
the casing is adapted to be held by the device body when the device body and the sensor electrode of the sensor located at the preset location at the head of the line are electrically connected via the connection structure, and
the device body includes an electrode to contact a part of the connection structure when the sensor cartridge is held by the device body,
wherein the connection structure is provided within the casing so as not to be exposed to the outside of the casing.

* * * * *